(12) United States Patent
Chousky

(10) Patent No.: US 11,395,843 B2
(45) Date of Patent: Jul. 26, 2022

(54) COMPOSITION AND METHOD FOR FORMING A COMPOSITION FOR INCREASING DERMAL NITRIC OXIDE

(71) Applicant: Spinal Relief Centres of Canada, Toronto (CA)

(72) Inventor: Cary Chousky, Toronto (CA)

(73) Assignee: Spinal Relief Centres of Canada, Toronto (CA)

( * ) Notice: Subject to any disclaimer, the term of this patent is extended or adjusted under 35 U.S.C. 154(b) by 0 days.

(21) Appl. No.: 16/672,408

(22) Filed: Nov. 1, 2019

(65) Prior Publication Data

US 2021/0052681 A1  Feb. 25, 2021

(51) Int. Cl.

| | |
|---|---|
| A61K 36/00 | (2006.01) |
| A61K 36/21 | (2006.01) |
| A61K 36/886 | (2006.01) |
| A61K 36/9066 | (2006.01) |
| A61K 36/76 | (2006.01) |
| A61K 36/8962 | (2006.01) |
| A61K 47/44 | (2017.01) |
| A61K 36/81 | (2006.01) |
| A61K 47/10 | (2017.01) |
| A61K 47/14 | (2017.01) |
| A61K 9/00 | (2006.01) |
| A61K 36/31 | (2006.01) |

(52) U.S. Cl.
CPC ............ *A61K 36/21* (2013.01); *A61K 9/0014* (2013.01); *A61K 36/31* (2013.01); *A61K 36/76* (2013.01); *A61K 36/81* (2013.01); *A61K 36/886* (2013.01); *A61K 36/8962* (2013.01); *A61K 36/9066* (2013.01); *A61K 47/10* (2013.01); *A61K 47/14* (2013.01); *A61K 47/44* (2013.01)

(58) Field of Classification Search
CPC ...................................................... A61K 36/00
See application file for complete search history.

(56) References Cited

U.S. PATENT DOCUMENTS

| | | | |
|---|---|---|---|
| 2005/0261367 A1* | 11/2005 | Murad | ............... A61Q 19/00 514/561 |
| 2007/0065473 A1 | 3/2007 | Miller | |
| 2007/0243132 A1 | 10/2007 | Russell-Jones et al. | |
| 2008/0193385 A1 | 8/2008 | Maibach | |
| 2009/0297634 A1 | 12/2009 | Friedman et al. | |
| 2015/0132345 A1 | 5/2015 | Av-Gay et al. | |
| 2018/0263944 A1 | 9/2018 | Tripp et al. | |

\* cited by examiner

*Primary Examiner* — Rosanne Kosson
(74) *Attorney, Agent, or Firm* — Orin Del Vecchio

(57) ABSTRACT

A composition for increasing dermal nitric oxide comprises in combination, a quantity of beet root extract, a quantity of aloe vera extract, a quantity of willow bark extract and a quantity of curcumin powder suspended in a base suitable for application to the skin of a user. The composition may be formed by providing the base suitable for application to the skin of a user and suspending within the base, in combination, a quantity of beet root extract, a quantity of aloe vera extract, a quantity of willow bark extract and a quantity of curcumin powder.

16 Claims, No Drawings

COMPOSITION AND METHOD FOR FORMING A COMPOSITION FOR INCREASING DERMAL NITRIC OXIDE

BACKGROUND OF THE INVENTION

1. Field of Invention

The present invention relates to topical creams in general and in particular to a topical cream useful for increasing dermal nitric oxide in a user.

2. Description of Related Art

The role of nitric oxide (NO) in regulating body circulation has become better understood in recent years. In particular, it has been shown that NO is effective and important many body functions, and in particular in vasodilation. Increasing vasodilation is an important significant for many resulting health conditions, including reducing inflammation, preventing and repairing wounds, diabetes and erectile dysfunction.

In particular, NO is a potent vasodilator synthesized and released by vascular endothelial cells and plays an important role in regulating vascular local resistance and blood flow. In mammalian cells, NO is principally produced along with L-citruilline by the enzymatic oxidation of L-arginine. Nitric oxide is also involved in the inhibition of both platelet and leukocyte aggregation and adhesion, the inhibition of cell proliferation, the scavenging of superoxide radicals and the modulation of endothelial layer permeability. Nitric oxide also has been shown to possess anti-microbial properties.

Currently one method of increasing NO in a body has been through the use of L-arginine. However L-arginine may cause significant side effects in an individual and also has limited effectiveness in individuals with impaired NO generation and/or diabetic neuropathy. L-arginine is also required to be taken internally thereby distributing the effects throughout the body as opposed to focusing such effects where they may be most beneficial. It will also be appreciated that such oral consumption of L-arginine may delay the effects increasing local NO.

SUMMARY OF THE INVENTION

According to a first embodiment of the present invention there is disclosed a composition for increasing dermal nitric oxide comprising, in combination, a quantity of beet root extract, a quantity of aloe vera extract, a quantity of curcumin powder and an acidifying agent suspended in a base suitable for application to the skin of a user.

The acidifying agent may comprises a quantity of willow bark extract. The willow bark extract may be present in an amount between 2 and 3% by weight. The base may be formed from a base oil selected from the group consisting of low molecular weight polyethylene glycol, polysorbate-20, polyacrylic acid polymers, primorose oil, castor oil, garlic oil, menthol and vitamin E oil.

The beet root extract may be present in an amount between 0.1 and 19.075% by weight. The aloe vera extract may be present in an amount between 2 and 3% by weight. The curcumin powder may be present in an amount between 0.5 and 1.5% by weight. The composition may further comprise at least one additional NO stimulating component selected from the group consisting of turnip root extract, capsaicin powder, garlic extract and spinach extract.

According to a further embodiment of the present invention there is disclosed a method of preparing a topical composition for increasing dermal nitric oxide comprising the steps of providing a base suitable for application to the skin of a user and suspending within the base, in combination, a quantity of beet root extract, a quantity of aloe vera extract, a quantity of curcumin powder and an acidifying agent.

The acidifying agent may comprises a quantity of willow bark extract. The willow bark extract may be present in an amount between 2 and 3% by weight. The base may be formed from a base oil selected from the group consisting of low molecular weight polyethylene glycol, polysorbate-20, polyacrylic acid polymers, primorose oil, castor oil, garlic oil, menthol and vitamin E oil.

The beet root extract may be present in an amount between 0.1 and 19.075% by weight. The aloe vera extract may be present in an amount between 2 and 3% by weight. The curcumin powder may be present in an amount between 0.5 and 1.5% by weight. The method may further comprise at least one additional NO stimulating component selected from the group consisting of turnip root extract, capsaicin powder, garlic extract and spinach extract.

Other aspects and features of the present invention will become apparent to those ordinarily skilled in the art upon review of the following description of specific embodiments of the invention in conjunction with the accompanying figures.

DETAILED DESCRIPTION

The present invention relates to a new plant based nitrates/nitrites and use thereof contained within a delivery system which allows passage into to the skin where such donors can be converted to Nitric Oxide to be used as a treatment for Diabetic Neuropathy, reduce pain, ischaemic ulceration, to promote wound healing and associated conditions. In particular, it has been surprisingly found that topical application to the skin of nitrates/nitrites at concentrations of up to 20% in an inert carrier cream or ointment reacts to produce oxides of nitrogen to cause the release of nitric oxides leading to sustained vasodilation of the microcirculatory blood vessels, without significant inflammation.

According to a first aspect of the invention there is provided the use of an acceptable acidifying agent, an acceptable source of plant based nitrate/nitrite ions or a nitrite precursor therefore in the preparation of an agent for the treatment of skin ischaemia and associated conditions.

The acceptable acidifying agent is adapted to reduce the pH at the site of application and can include any suitable organic acid such as ascorbic acid (vitamin C), salicylic acid, acetyl salicylic acid, acetic acid or a salt or a derivative thereof in a concentration up to 20% w/w, suitably 0.25 to 10% w/w, preferably 4 to 6% w/w. A particularly preferred concentration is 4% or 5% w/w. The preferred pH range is from pH2 to pH7, preferably pH4. Other acidifying agents include but are not limited to, ammonium or aluminium salts, phenol, benzoic acid. Inorganic acids such as hydrochloric acid may be used if sufficient dilute and/or appropriately buffered. The acidifying agent may be present as a dissolved salt or in a liquid form. In the present composition, the acid is provided in the form of salicylic acid obtained from the willow bark although other organic acids may be utilized as well, such as, by way of non-limiting example, from vitamin c.

The pharmacologically acceptable source of nitrate/nitrite ions would come from Beet root, turnip root, spinach, Garlic. The concentration of the nitrate/nitrite ion source may be up to 20% w/w, suitably 0.25 to 10%, preferably 4 to 15%. A particularly preferred concentration is 19% or 20% w/w.

Suitably, the final nitrite ion concentration present in the composition is up to 20% w/w, generally in the range of from 0.25% to 20% w/w A particularly preferred nitrite ion concentration is 19 or 20% w/w.

According to the first embodiment of the present invention, there is disclosed a composition for increasing nitric oxide (NO) in a user. The composition comprises a base suitable for application to the skin of a user and a plurality of NO stimulating components and at least one acidifying agent which will in combination stimulate the skin of a user to synthesize and release NO in the dermis. The plurality of NO stimulating components may be selected from beet root extract, turnip root extract, garlic oil and spinach extract, Capsaicin and Menthol. It has been found that in the combinations and quantities setout herein, enhanced NO synthesis has been achieved in the dermis.

The base may be any suitable, spreadable liquid, gel or cream which may be applied to the skin of a user. In particular, the base may be formed of a one or more of low molecular weight polyethylene glycol, such as, by way of non-limiting example, PEG 400, polysorbate 20, polyacrylic acid polymers, primrose oil, castor oil, menthol and vitamin E oil. In practice it has been found that the polysorbate 20 marketed under the trade name Tween® 20 and the polyacrylic acid polymer marketed under the trade name Carbopo® have been useful. It will also be appreciated that some base materials such as, by way of non-limiting example, menthol will be less desirable where the composition is to be applied to sensitive areas of a body such as for use as an erectile dysfunction aid. Other components may be added to the composition for additional purposes, such as, by way of non-limiting example, aloe vera to aid in pain relieving, anti-oxidant and anti bacterial properties. Willow bark extract may provide analgesic and anti-inflammatory properties. Curcumin may provide anti-inflammatory and anti-oxidant properties. Capsaicin may provide pain reducer/analgesic properties and menthol may provide analgesic properties.

The composition may be spread or otherwise applied to the skin of a user whereupon it will be absorbed therein. The NO stimulating components will then enhance and stimulate the production of NO In the dermis of the user resulting in increased vascular dilation at that region. It will be appreciated that such increased vascular dilation will increase blood flow locally which may be useful for treating a wide range of disorders and conditions, including but not limited to diabetes, lupus, rheumatoid arthritis, scleroderma, psoriasis, venus insufficiency, erectile dysfunction, pain management, repair nerve damage, prevent wounds, reduce pain and manage diabetic neuropathy.

As used herein, an "essential oil" is any hydrophobic liquid containing volatile aromatic compounds from plants. They are also known as volatile or ethereal oils, or simply as the "oil of" the plant material from which they were extracted, such as oil of grapefruit. The term "essential" indicates that the oil carries distinctive scent (essence) of the plant. Essential oils are may be extracted or prepared by any known method but are typically extracted by distillation and hence may be concentrated. Other processes include expression and solvent extraction. Furthermore, as used throughout the specification the term "about" is defined to include a range to each side of that value as to provide a clinically insignificant differences which will vary from component to component.

In some embodiments, the compositions and formulations of the present invention may contain beet root extract. Beet root extract may be obtained from the root of the beet plant (*Beta vulgaris*) by commonly known methods. In particular it has been found that dry extracts of the beet root obtained by commonly known methods have been particularly useful for the present compositions. According to the present invention, beet root extract may be present in the compositions of the present invention from about 0.1% by weight to about 19.075% by weight, although it will be appreciated that other quantities may be utilized as well.

In some embodiments, the compositions and formulations of the present invention may contain garlic Oil. Garlic oil may be obtained from the garlic plant (*Allium sativum*) by commonly known methods. According to the present invention, garlic oil may be present in the compositions of the present invention from about 2% by weight to about 3% by weight, although it will be appreciated that other quantities may be utilized as well.

In some embodiments, the compositions and formulations of the present invention may contain curcumin powder. Curumin powder may be obtained from the Curcuma Longa plants by commonly known methods. According to the present invention, curcumin powder may be present in the compositions of the present invention from about 0.5% by weight to about 1.5% by weight, although it will be appreciated that other quantities may be utilized as well.

In some embodiments, the compositions and formulations of the present invention may contain aloe vera extract. Aloe vera extract may be obtained from the aloe vera plant (*Aloe barbadensis*) by commonly known methods. In particular it has been found that dry extracts of the aloe vera plant obtained by commonly known methods have been particularly useful for the present compositions. According to the present invention, aloe vera extract may be present in the compositions of the present invention from about 2% by weight to about 3% by weight, although it will be appreciated that other quantities may be utilized as well.

In some embodiments, the compositions and formulations of the present invention may contain willow bark extract. Willow bark extract may be obtained from the bark of the willow tree (*Salix alba*) by commonly known methods. In particular it has been found that dry extracts of willow bark obtained by commonly known methods have been particularly useful for the present compositions. According to the present invention, willow bark extract may be present in the compositions of the present invention from about 2% by weight to about 3% by weight, although it will be appreciated that other quantities may be utilized as well.

In some embodiments, the compositions and formulations of the present invention may contain spinach extract. Spinach extract may be obtained from the whole spinach plant (*Spinacia oleracea*) by commonly known methods. In particular it has been found that dry extracts spinach obtained by commonly known methods have been particularly useful for the present compositions. According to the present invention, spinach extract may be present in the compositions of the present invention from about 3% by weight to about 4.5% by weight, although it will be appreciated that other quantities may be utilized as well.

In some embodiments, the compositions and formulations of the present invention may contain capsaicin powder. Capsaicin powder may be obtained from the fruit of the Capsicum annum plant by commonly known methods.

According to the present invention, capsaicin powder may be present in the compositions of the present invention from about 0.025% by weight to about 0.1% by weight, although it will be appreciated that other quantities may be utilized as well.

In some embodiments, the compositions and formulations of the present invention may contain turnip extract. Turnip extract may be obtained from the root of the turnip plant (*Brassia rapa*) by commonly known methods. In particular it has been found that dry extracts of the beet root obtained by commonly known methods have been particularly useful for the present compositions. According to the present invention, turnip root extract may be present in the compositions of the present invention from about 0.5% by weight to about 9% by weight, although it will be appreciated that other quantities may be utilized as well.

EXAMPLES

The following examples will provide an illustration of the use of the present composition. The present compositions set out in Examples 1-4 were mixed within a base material having the following non-medical ingredients:

TABLE 1

| Base Non-Medicinal Ingredients (base): | | |
|---|---|---|
| Common Name | Form | Weight (%) |
| Menthol | Base Oil | 1.0 |
| Garlic | Base Oil | 1.0 |
| Castor Oil | Base Oil | 1.5 |
| Camphor | Crystal | 0.4 |
| Vitamin E | Base Oil | 0.3 |
| Base | Base | 69.3 |

Example 1

The composition was prepared in the following percentages by weight:

TABLE 2

| Composition 1 | | |
|---|---|---|
| Common Name | Form | Weight (%) |
| Beet root | Dry Extract | 10.5 |
| Turnip | Dry Extract | 9.0 |
| Capsaicin | Powder | 0.1 |
| *Aloe vera* | Dry Extract | 3.0 |
| Willow | Dry Extract | 3.0 |
| Curcumin | Powder | 0.9 |

The above composition has been found to be particularly useful for reducing pain and increasing Nitric Oxide concentrations in dermal and serum of people suffering from peripheral neuropathy in a diabetic population.

Example 2

The composition was prepared in the following percentages by weight:

TABLE 3

| Composition 2 | | |
|---|---|---|
| Common Name | Form | Weight (%) |
| Beet root | Dry Extract | 15.025 |
| Turnip | Dry Extract | 4.5 |
| Capsaicin | Powder | 0.075 |
| *Aloe vera* | Dry Extract | 3.0 |
| Willow | Dry Extract | 3.0 |
| Curcumin | Powder | 0.9 |

The above composition has been found to be particularly useful for reducing pain and increasing Nitric Oxide concentrations in dermal and serum of people suffering from peripheral neuropathy in a diabetic population.

Example 3

The composition was prepared in the following percentages by weight:

TABLE 4

| Composition 3 | | |
|---|---|---|
| Common Name | Form | Weight (%) |
| Beet root | Dry Extract | 17.05 |
| Turnip | Dry Extract | 2.5 |
| Capsaicin | Powder | 0.05 |
| *Aloe vera* | Dry Extract | 3.0 |
| Willow | Dry Extract | 3.0 |
| Curcumin | Powder | 0.9 |

The above composition has been found to be particularly useful for reducing pain and increasing Nitric Oxide concentrations in dermal and serum of people suffering from peripheral neuropathy in a diabetic population.

Example 4

The composition was prepared in the following percentages by weight:

TABLE 5

| Composition 4 | | |
|---|---|---|
| Common Name | Form | Weight (%) |
| Beet root | Dry Extract | 19.075 |
| Turnip | Dry Extract | 0.5 |
| Capsaicin | Powder | 0.025 |
| *Aloe vera* | Dry Extract | 3.0 |
| Willow | Dry Extract | 3.0 |
| Curcumin | Powder | 0.9 |

The above composition has been found to be particularly useful for reducing pain and increasing Nitric Oxide concentrations in dermal and serum of people suffering from peripheral neuropathy in a diabetic population.

The present compositions set out in Examples 5-7 were mixed within a base material having the following non-medical ingredients:

TABLE 6

Base
Non-Medicinal Ingredients (base):

| Common Name | Form | Weight (%) |
|---|---|---|
| Primrose Oil | Base Oil | 1.0 |
| Castor Oil | Base Oil | 1.5 |
| Camphor | Crystal | 1.5 |
| Vita | Crystal | 1.0 |
| Base | Base | 68 |

Example 5

The composition was prepared in the following percentages by weight:

TABLE 7

Composition 5

| Common Name | Form | Weight (%) |
|---|---|---|
| Beet root | Dry Extract | 14 |
| Garlic | Oil | 3.0 |
| Curcumin | Powder | 1.5 |
| Aloe vera | Dry Extract | 2.0 |
| Willow | Dry Extract | 2.0 |
| Spinach | Dry Extract | 4.5 |

The above composition has been found to be particularly useful for increasing Nitric Oxide levels in skin and serum in a Diabetic Population.

Example 6

The composition was prepared in the following percentages by weight:

TABLE 8

Composition 6

| Common Name | Form | Weight (%) |
|---|---|---|
| Beet root | Dry Extract | 16 |
| Garlic | Oil | 2.5 |
| Curcumin | Powder | 1.0 |
| Aloe vera | Dry Extract | 2.0 |
| Willow | Dry Extract | 2.0 |
| Spinach | Dry Extract | 3.5 |

The above composition has been found to be particularly useful for increasing Nitric Oxide levels in skin and serum in a Diabetic Population.

Example 7

The composition was prepared in the following percentages by weight:

TABLE 9

Composition 7

| Common Name | Form | Weight (%) |
|---|---|---|
| Beet root | Dry Extract | 17.5 |
| Garlic | Oil | 2.0 |
| Curcumin | Powder | 0.5 |
| Aloe vera | Dry Extract | 2.0 |

TABLE 9-continued

Composition 7

| Common Name | Form | Weight (%) |
|---|---|---|
| Willow | Dry Extract | 2.0 |
| Spinach | Dry Extract | 3.0 |

The above composition has been found to be particularly useful for increasing Nitric Oxide levels in skin and serum in a Diabetic Population.

Optionally, natural composition comprising NO stimulating components in an inert carrier cream or ointment for its anti-microbial properties. This activity could be further used against patients with fungal infection of the feet ("Athlete's Foot" ortidea pedis).

While specific embodiments of the invention have been described and illustrated, such embodiments should be considered illustrative of the invention only and not as limiting the invention as construed in accordance with the accompanying claims.

What is claimed is:

1. A composition for increasing dermal nitric oxide comprising, in combination, effective amount of (i) a quantity of beet root extract, (ii) a quantity of aloe vera extract, (iii) a quantity of curcumin powder and (iv) an acidifying agent, all suspended in a base, wherein the composition is formulated for application to the skin of a user.

2. The composition of claim 1 wherein said acidifying agent comprises a quantity of willow bark extract.

3. The composition of claim 2 wherein said willow bark extract is present in an amount between 2 and 3% by weight.

4. The composition of claim 1 wherein said base is formed from a base oil selected from the group consisting of low molecular weight polyethylene glycol, polysorbate-20, polyacrylic acid polymers, primorose oil, castor oil, garlic oil, menthol and vitamin E oil.

5. The composition of claim 1 wherein said beet root extract is present in an amount between 0.1 and 19.075% by weight.

6. The composition of claim 1 wherein said aloe vera extract is present in an amount between 2 and 3% by weight.

7. The composition of claim 1 wherein said curcumin powder is present in an amount between 0.5 and 1.5% by weight.

8. The composition of claim 1 further comprising at least one additional NO stimulating component selected from the group consisting of turnip root extract, capsaicin powder, garlic extract and spinach extract.

9. A method of preparing a topical composition for increasing dermal nitric oxide comprising the steps of:
a) providing a base suitable for application to the skin of a user; and
b) suspending within said base, in combination, effective amounts of (i) a quantity of beet root extract, (ii) a quantity of aloe vera extract, (iii) a quantity of curcumin powder and (iv) an acidifying agent.

10. The method of claim 9 wherein said acidifying agent comprises a quantity of willow bark extract.

11. The method of claim 10 wherein said willow bark extract is present in an amount between 2 and 3% by weight.

12. The method of claim 9 wherein said base is formed from a base oil selected from the group consisting of low molecular weight polyethylene glycol, polysorbate-20, polyacrylic acid polymers, primorose oil, castor oil, garlic oil, menthol and vitamin E oil.

13. The method of claim 9 wherein said beet root extract is present in an amount between 0.1 and 19.075% by weight.

14. The method of claim 9 wherein said aloe vera extract is present in an amount between 2 and 3% by weight.

15. The method of claim 9 wherein said curcumin powder is present in an amount between 0.5 and 1.5% by weight.

16. The method of claim 9 further comprising at least one additional NO stimulating component selected from the group consisting of turnip root extract, capsaicin powder, garlic extract and spinach extract.

* * * * *